United States Patent [19]

Raehse et al.

[11] Patent Number: 4,751,003
[45] Date of Patent: Jun. 14, 1988

[54] CROSSFLOW MICROFILTRATION PROCESS FOR THE SEPARATION OF BIOTECHNOLOGICALLY PRODUCED MATERIALS

[75] Inventors: Wilfried Raehse, Duesseldorf; Franz-Josef Carduck; Norbert Kuehne, both of Haan, all of Fed. Rep. of Germany

[73] Assignee: Henkel Kommanditgesellschaft auf Aktien, Duesseldorf, Fed. Rep. of Germany

[21] Appl. No.: 858,408

[22] Filed: May 1, 1986

[30] Foreign Application Priority Data

May 2, 1985 [DE] Fed. Rep. of Germany ....... 3515650

[51] Int. Cl.⁴ .................. B01D 13/00; C12N 9/48; C12N 9/50

[52] U.S. Cl. .................. 210/639; 210/641; 210/651; 210/653; 435/212; 435/219; 435/222; 435/814

[58] Field of Search .............. 210/651, 641, 650, 638, 210/639, 500.41, 653, 805, 806; 435/803, 212, 261, 219-222, 813-816

[56] References Cited

U.S. PATENT DOCUMENTS 4,191,182  3/1980  Popovich et al. .
4,212,742  7/1980  Solomon et al. .
4,420,398  12/1983  Castino ........................ 210/641

FOREIGN PATENT DOCUMENTS 3005605  10/1981  Fed. Rep. of Germany .

OTHER PUBLICATIONS

Rautenbach, Robert, and Rainer Albrecht, *Membrantrennver-Faitren Ultrafiltration and Umkemrosmose*, 1981, Otto Salle Verlag EmpH and Co., Frankfurt, 5 pages.

Dytnerskij, Vonju. I., *Membranprozesse Zur Trennung Flussiger Gemische*, 1977, pp. 5, 18, 19, 22, 23, 120, 121, 129, Veb Deutscher Verlas, Leipzig.

Schweitzer, Philip A., Editor, *Handbook of Separation Techniques for Chemical Engineers*, 1979, pp. 2-80, 2-84 and 2-85, McGraw-Hill Book Co., N.Y.

Kroner, K. H. et al., "Problems and Improvements of Cross-Flow-Filtration in Enzyme Recovery Processes", Third Eurp. Cong. on Biotechnology, Munich 1984, vol. 3, pp. III—549 to 555.

"Development Studies of Crossflow Microfiltrations," R. Bertera, H. Steven, M. Metcalfe, The Chemical Engineer, Jun. 1984, pp. 10, 11, 13 and 14.

"Mikrofiltration Von Fermenterbruhen" Chem. Ing. Tech., 57, (1985), No. 9, pp. 747-753; Raehse and Carduck.

"Tangential Flow Filtration–A New Method for the Separation of Bacterial Enzymes From Cell Debris" (1983), vol. 5, No. 4, pp. 277-282 in Biotechnology Letters.

*Primary Examiner*—Benoit Castel
*Attorney, Agent, or Firm*—Ernest G. Szoke; Henry E. Millson, Jr.; Mark A. Greenfield

[57] ABSTRACT

The invention relates to a process for the separation of biotechnologically produced valuable materials form a cell suspension by crossflow microfiltration to obtain an high specific permeate flux while retention stays near 0% for long periods. To enable crossflow microfiltration to be carried out on an industrial scale in biotechnology in the separation of biotechnologically produced extracellular valuable materials from a cell suspension, particularly in the separation of alkaline protease for recovering enzyme, under economically acceptacle conditions, alkaline protease of relatively high molecular weight, more especially enzyme >20,000 daltons, is separated from a fermenter solution using polysulfone tubes having micropore diameters of from 0.3 to 0.5 μm at a rate of flow of the fermenter solution of from 3 to 6 m/s parallel to the membrane surface and with a pressure difference between the concentrate side and the permeate side of 2 bar, the ratio of the mean pore diameter of the membrane to the size of the microorganisms remaining in the concentrate being between 0.15 and 0.85

11 Claims, 1 Drawing Sheet

CROSSFLOW MICROFILTRATION PROCESS FOR THE SEPARATION OF BIOTECHNOLOGICALLY PRODUCED MATERIALS

BACKGROUND OF THE INVENTION

1. Field of the Invention

This invention relates to a process for the separation of biotechnologically produced valuable materials from a cell suspension by crossflow microfiltration using porous polymeric tubes with micropores >0.1 μm as membranes through which the fermenter solution flows at a rate of >2 m/s, a pressure difference of less than 5 bar prevailing between the concentrate side and the permeate side.

2. Description of Related Art

A fairly recent development in the field of solid/liquid separation is crossflow microfiltration ("Development Studies of Crossflow Microfiltration", R. Bertera, H. Steven, M. Metcalfe, The Chemical Engineer, June 1984, pp. 10 et seq).

One of the potential applications of this membrane microfiltration technique is in the separation of extracellular valuable materials, particularly those of relatively high molecular weight, from cell bodies and other solids.

This separation in culture and nutrient solutions such as for example fermenter solutions, of dissolved extracellular valuable materials from cells, cell fragments and other solids emanating from the nutrient medium is extremely problematical on account of the microsize of the solids and bacterial cell to be retained which vary from 0.2 to 5 μm in size, the small difference in density between the fermenter solution and the solids and bacterial cells to be separated off, the compressibility of the solids and bacterial cells and the frequently non-Newtonian flow behavior of the relatively high viscosity fermenter solutions.

Accordingly, conventional solid/liquid separation techniques and equipment, such as filtration and centrifuging using, for example, high-performance separators or filtration units, are still being used in industry although they are at the limit of economy and perform very inefficiently in this field of biotechnology.

At the present time, very few technical applications going beyond the laboratory scale, for example the thickening of suspension or the separation of emulsions, are known for the technique of crossflow microfiltration suitable for the separation of dissolved substances of relatively high molecular weight.

The industrial application of crossflow microfiltration for the separation or rather isolation of extracellular materials of relatively high molecular weight from culture or fermenter solutions, such as for example the isolation of alkaline protease for the recovery of enzymes, is attended by the difficulties described above. However, the main problem involved in the commercial operation of the crossflow microfiltration technique in this biotechnical application is the surface layer forming on the surface of the membrane which, in view of the concentration polarization, prevents the passage of the valuable materials through the membrane and hence causes retention (holding back of the valuable materials) and limits the flow of permeate. It is particularly with liquids of relatively high solids content that this surface layer forms and clogs the membrane pores very quickly, retention reaching levels of around 100% after only a short time, so that the membrane becomes impermeable to the materials. In order to make the membranes repermeable to the materials, the basically continuous process has to be interrupted for cleaning to be carried out.

Of particular interest may be U.S. Pat. No. 4,420,398-Castino, which describes the crossflow ultrafiltration of cell-produced biological by-products having molecular weights of including 15,000 to 70,000 daltons. Crossflow filtration is also described in U.S. Pat. Nos. 4,191,182-Popovich, et al., and 4,212,742-Solomon, et al.

SUMMARY OF THE INVENTION

It has now been found that enzymes greater than 20,000 daltons can be separated from a fermentation or fermenter solution, liquor or broth by using polysulfone tubes or membranes having micropore diameters of from about 0.3 to about 0.5 μm, a rate of flow of the fermentation broth from about 3 to 6 m/s parallel to the membrane surface with a pressure difference between the concentrate side and permeate side of about 2 bar, and in which the ratio of the mean pore diameter to the size of the microorganisms remaining in the concentrate is between about 0.15 and about 0.85. Under these conditions a high permeate flow rate or flux can be maintained while at the same time retention stays near 0%.

Accordingly, the present inventon obtains a high specific permeate flux while at the same time, retention stays near 0% for as long as possible to facilitate the application of large-scale crossflow microfiltration in biotechnology for the separation of biotechnologically prepared extracellular valuable materials from a cell suspension and more especially for the separation of alkaline protease for recovering enzyme under economically satisfactory conditions.

According to the invention, this is achieved in that alkaline protease of relatively high molecular weight, more especially an enzyme of >20,000 daltons, is separated from a fermenter solution using polysulfone tubes having micropore diameters of from 0.3 to 0.5 μm at a rate of flow of the fermenter solution of from 3 to 6 m/s parallel to the membrane surface and with a pressure difference between the concentrate side and the permeate side of 2 bar, the ratio of the mean pore diameter of the membrane to the size of the microorganisms remaining in the concentrate being between 0.15 and 0.85.

The process according to the invention facilitates the industrial application of crossflow microfiltration, i.e. the application of crossflow microfiltration in biotechnological separation plants with a filter or membrane area of generally more than 10 m$^2$, under economically and technologically acceptable conditions. More particularly, specific permeate flux and retention behavior are distinctly improved in the application of crossflow microfiltration in the above-mentioned biotechnological field. This is achieved in particular by the inventive combination of the specific choice of the material polysulfone, the micropores with mean pore diameters of from about 0.3 to about 0.5 μm, the flow rate of from 3 to 6 m/s, and the pressure difference of about 2 bar.

BRIEF DESCRIPTION OF THE DRAWINGS

One embodiment of the invention is described by way of example in the following with reference to the accompanying drawings, wherein.

DETAILED DESCRIPTION AND PREFERRED EMBODIMENTS

Figure 1:
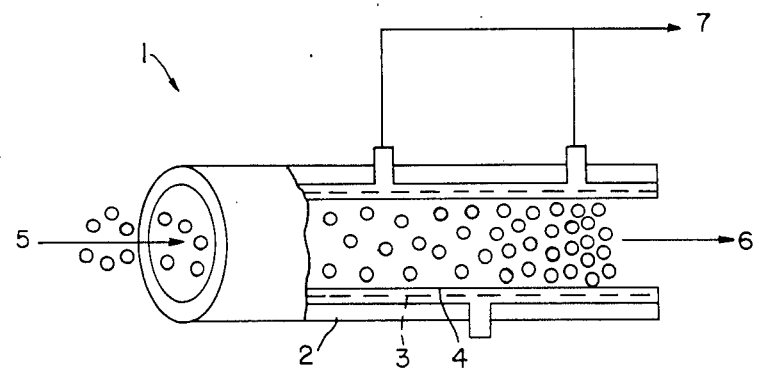
FIG. 1 illustrates the principle of crossflow microfiltration for the separation or rather isolation of extracellular ingredients from culture or fermenter solutions.

The process for separating biotechnologically produced extracellular valuable materials from a cell suspension by crossflow microfiltration can be illustrated by reference to the drawings in which the process uses a tubular separation modular 1. The tubular separation module 1 consists of a support tube 2 into which is fitted a carrier tube 3 of polyester cloth to the inner surface of which a separation-active, ca. 50 to 100 $\mu$m thick membrane layer 4 of polysulfone is applied. The tubular separation module 1 has diameters of from 5 to 15 mm.

The culture of fermenter solution of broth is passed across the separation-active membrane layer 4 in the arrowed direction at flow rates of from 3 to 6 m/s, the valuable materials penetrating through the separation-active membrane layer 4 in the radial direction while cells, cell fragments and solids are held back by the separation-active membrane layer 4. A liquid concentrate 6 containing the cells, cell fragments and solids and a liquid permeate 7 containing the valuable material separated off is formed. A pressure gradient acts as the driving force for the passage of liquid of the fermenter solution 5 and the valuable materials dissolved therein through the separation-active membrane layer 4. The mean pressure gradient between the concentrate side and the permeate side is 2 bar. The atmospheric pressure and the geodetic height of the open runoff prevail on the permeate side. The separation-active membrane layer 4 of polysulfone contains micropores having a mean pore diameter of from 0.3 to 0.5 $\mu$m. The ratio of this mean pore diameter of the membrane 4 to the size of the microorganisms, (more especially bacterial cultures, which are capable of growth both in the presence of sodium azide and in the presence of sodium chloride even at temperatures around 55° C.) which remain in the concentrate 6, having been previously introduced with the culture or fermenter solution 5, is from 0.15 to 0.85.

The permeate separated off is in particular an alkaline protease in which an enzyme having a molecular weight of greater than 20,000 daltons represents the valuable material to be recovered.

Figure 2:
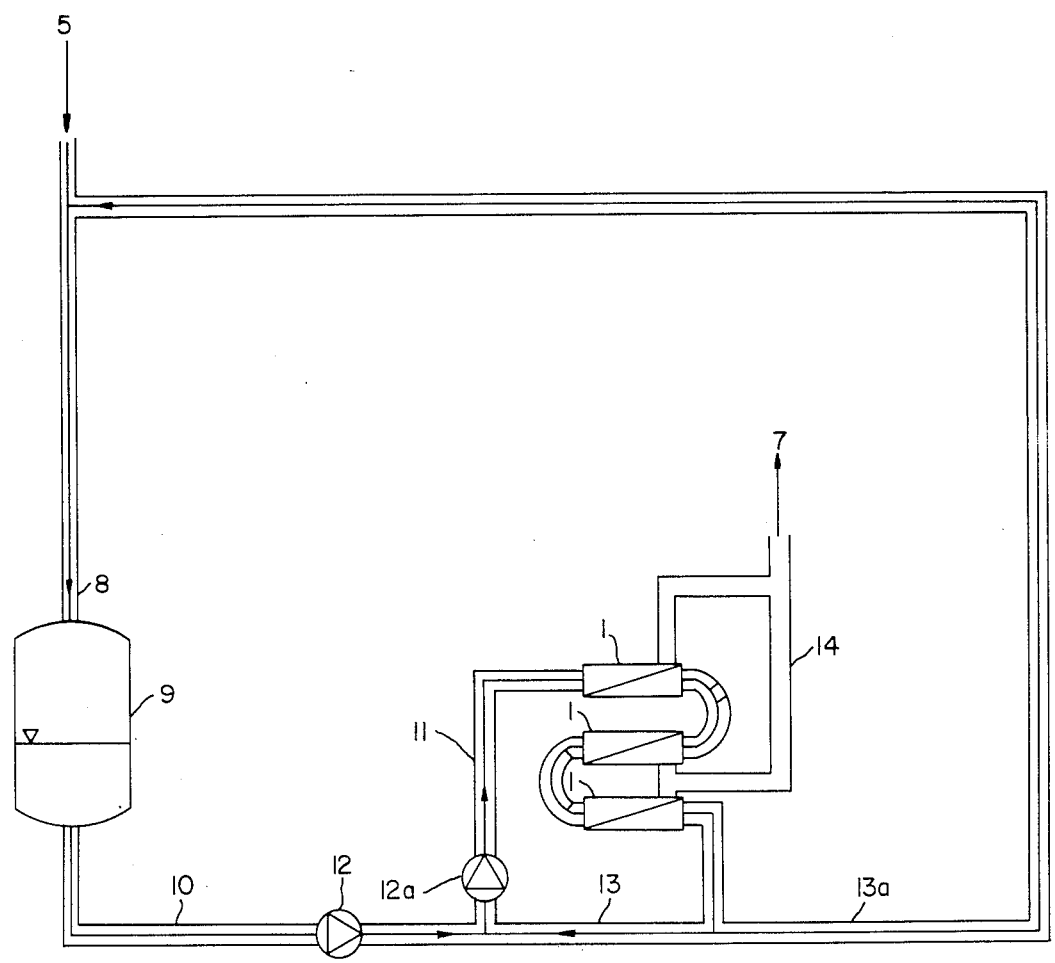
FIG. 2 is a simplified flow diagram of a crossflow microfiltration system.

The tubular separation module 1 is the heart of the simplified flow diagram of a crossflow microfiltration system shown in FIG. 2. The fermenter solution 5 is delivered through a conduit 8 into a heatable hold tank 9 from which it is pumped by pumps 12 and 12a through conduits 10 and 11, respectively, into the tubular separation modules 1. Three tubular separation modules 1 arranged one behind the other form a separation stage. In the first two of the three tubular separation modules 1, the culture or fermenter solution 5 is separated into the concentrate 6 and the permeate 7, the concentrate entering the next module 1 through conduits, and being largely recycled from the last module into the feed line 11 through the conduit 13 while the permeate from each separation module 1 flows into the discharge conduit 14. A relatively small part of the concentrate 6 passes back into the tank 9 through a branch conduit 13a and the conduit 8, for which purpose the output of the pump 12a is adjusted to a correspondingly higher level than that of the pump 12.

In other embodiments, the permeate 7 may be delivered through the discharge conduit 14 to a reprocessing system, such as an ultrafiltration system, to enrich the valuable materials.

The permeate may also be delivered to the conduits 10 or 11 through a branch of the discharge conduit 14, optionally with a collecting tank in between, for carrying out cleaning cycles, in which case the flow of fermenter solution from the hold tank 9 is shut off.

It is of course also possible to carry out the crossflow microfiltration process with more than one separation stage consisting of separation modules 1 and with more than three successive separation modules 1. Neither is the process confined to the use of single hold tank 9.

In particular, it is also possible to equip the crossflow microfiltration process with a batch or continuous diafiltration module for the controlled feed of liquid to enable the concentrate 6 to be extracted with some of its ambient liquid and the amount of liquid entering the permeate to be compensated. In addition, the diameters of the separation modules 1 are not confined to the above-mentioned range of from 5 to 15 mm.

Polysulfone membranes are particularly suitable for use under the technical conditions of crossflow microfiltration by virtue of the permeate flow rate (flux) and retention values obtainable with them. Whereas, for example, tetrafluoroethylene microfiltration membranes, tubular polypropylene microfiltration membranes or ultrafiltration membranes provide inadequate permeate flux levels under the technical conditons of crossflow microfiltration and show retention values of more than 50% after only a short period of operation, corresponding polysulfone microfiltration membranes show retention values near 0% over distinctly longer periods of operation.

Pore size distribution in the polysulfone membranes characterized by the mean pore diameter is essential to optimal permeate flux and low retention. Accordingly, for the industrial application of crossflow microfiltration in the described field, it is essential that the micropores have mean pore diameter of from 0.3 to 0.5 $\mu$m, with the ratio of the mean pore diameter of the membranes to the size of the microorganisms remaining in the concentrate being frm 0.15 to 0.85. It is precisely these selected mean pore diameters of from 0.3 to 0.5 $\mu$m which ensure that retention stays near 0% over a period of operation of up to 24 hours. By contrast, it has been found that with significantly smaller pore diameters, retention reaches levels of higher than 40% after only three hours on account of the surface layer which accumulates. Where significantly larger micropores are selected, the pores become clogged after only a short period of operation on account of the bacterial cells remaining therein.

On account of the unsatisfactorily high retention levels of >40% for economically carrying out crossflow microfiltration, the basically continuous process of crossflow microfiltration normally has to be interrupted after only about three hours for cleaning to be conducted. In the process according to the invention, retention levels as high as these occur only after 24 hours, so that cleaning need only be carried out after that time. This considerably improves the economy of the process.

In addition, the rate of flow in the tubular polysulfone separation membranes is of considerable influence.

With the fermenter solutions used, low retention values can only be obtained at relatively high flow rates and, economically, only at flow rates of from 3 to 6 m/s. The main problem in this regard is the surface layer which builds up on the surface of the membrane and whose formation primarily can be avoided by turbulent flow conditions. In view of the viscosity conditions prevailing in a fermenter solution, turbulent flow conditions in the tubular membranes can best be established by high flow rates which, on the one hand, increase the Reynold's number and, on the other hand, keep the effective viscosity of the non-Newtonian liquid as low as possible by increasing the shear forces. In general, these flow conditions are only safely established at the beginning of crossflow microfiltration because, in the course of the process, an increase in concentration and a resulting increase in viscosity occur in particular through partly recycled fermenter or rather concentrate solution. On an industrial scale, however, flow rate cannot be increased indefinitely for economic and process-technological reasons, first because the pumping energy required increases with the third power of ten of the flow rate and second because energy introduced in the form of heat during the pumping operation has to be dissipated again through heat exchangers. Accordingly, the optimal flow rate change in tubular separation membranes in the separation of extracellular valuable materials on an industrial scale in the generic application of microfiltration is from 3 to 6 m/s.

In addition, it is technologically and economically practical to carry out the process with a mean pressure gradient between the concentrate side and the permeate side of about 2 bar. As the pressure gradient is increased to more than 2 bar, the polysulfone membrane suffers irreversible membrane compaction. By contrast, as the pressure gradient is reduced to below 2 bar, permeate flux is unnecessarily reduced.

The specific permeate flux may advantageously be improved by an addition of from 0.05 to 1% by weight of solids having a particle size of $\leq 500$ μm. Thus, permeate flux may be increased by a factor of two to three by addition of, for example, ground cellulose, particularly fibrous cellulose having particle sizes of $\leq 500$ μm in a quantity of from 0.05 to 1% by weight. This increase in permeate flux is noticeable above all after a certain period of operation, i.e. at relatively high concentrations, although the viscosity of the fermenter solution is still increasing through the addition of cellulose. The positive effect of the solid added is noticeable above all when turbulent flow conditions can no longer be maintained. Cellulose has proved the most suitable additive. Additions of other solids, such as for example sodium alumium silicate or iron hydroxide, do not produce an increase in permeate flux in the fermenter solutions in question. In addition, it is advisable to add surfactants to the fermenter solution to improve permeate flux and retention behaviour.

In another embodiment of the process according to the invention, the crossflow microfiltration is followed by an ultrafiltration to enrich the valuable material. In a following ultrafiltration unit, the valuable material dissolved in the permeate may advantageously be enriched or increased in concentration by being retained in the ultrafiltration unit using standard membranes while the remaining constituents of the permeate solution, such as for example water, salts and smaller molecules, are allowed through. The crossflow microfiltration and the ultrafiltration combined in this way form a favorable and simple process.

To obtain high retention values, it is desirable to adjust the pH value from 6.2 to 7.2 in the fermenter solution during crossflow microfiltration of the alkaline protease. Although higher pH values would be more favorable in regard to enzyme activity and the viscosity of alkaline protease, they are out of the question because, at pH values above 7.2, retention increases rapidly to unsatisfactorily high values.

Finally, the process according to the invention is distinguished by the fact that the crossflow microfiltration is economically carried out on an industrial scale in the separation of enzymes from bacterial cultures which are capable of growth both in the present of azide, particularly sodium azide, and in the presence of sodium chloride even at temperatures of 55° C.

We claim:

1. A crossflow microfiltration process for the separation of biotechnologically produced materials from a cell suspension comprising
   (A) passing a cell suspension containing biotechnologically produced materials through a tubular, polysulfone, polymeric, microfiltration membrane having an inner surface and an outer surface, in crossflow to said inner surface, wherein
      (a) said cell suspension flows through the tubular microfiltration membrane at about 3 to 6 meters per second,
      (b) said microfiltration membrane has micropores with a mean diameter of about 0.3 to 0.5 μm,
      (c) said mircopores are about 0.15 to 0.85 times the size of cells in said cell suspension, and
      (d) there is a mean pressure gradient of about 2 bar between the inner surface of said microfiltration membrane and its outer surface,
   so that the materials to be separated pass through said microfiltration membrane as a filtrate and the cell suspension remaining becomes a concentrate; and
   (B) recovering said filtrate.

2. The process of claim 1 wherein solids having a particle size of not more than 500 μm are added to said cell suspension in an amount effective to increase the flux of filtrate through said microfiltration membrane.

3. The process of claim 2 wherein about 0.05 to 1.0% by weight of solids are added, based upon the weight of said cell suspension.

4. The process of claim 3 wherein said solids are ground cellulose.

5. The process of claim 1 wherein said permeate is an alkaline protease.

6. The process of claim 1 wherein the pH of said cell suspension is adjusted to about 6.2 to 7.2 before microfiltration.

7. The process of claim 5 wherein a surfactant is added to said cell suspension before microfiltration.

8. The process of claim 1 wherein said permeate is an alkaline protease enzyme of more than 20,000 daltons.

9. The process of claim 1 further comprising serially passing said cell suspension through a plurality of the microfiltration membranes which are serially connected, and recycling cell suspension concentrate leaving the last of said plurality to the first of said plurality.

10. The process of claim 9 further comprising enriching the recovered filtrate by subjecting it to ultrafiltration.

11. The process of claim 1 further comprising enriching the recovered filtrate by subjecting it to ultrafiltration.

* * * * *